United States Patent [19]
Ring et al.

[11] Patent Number: 4,588,400
[45] Date of Patent: May 13, 1986

[54] LIQUID LOADED PAD FOR MEDICAL APPLICATIONS

[75] Inventors: David F. Ring, Skillman; Wilson Nashed, North Brunswick; Thurman Dow, Somerville, all of N.J.

[73] Assignee: Johnson & Johnson Products, Inc., New Brunswick, N.J.

[21] Appl. No.: 450,324

[22] Filed: Dec. 16, 1982

[51] Int. Cl.⁴ .............................................. A61F 13/00
[52] U.S. Cl. .................................... 604/304; 604/289; 604/897; 128/156; 424/28; 514/781
[58] Field of Search ............... 604/289, 304, 307, 308, 604/358, 365, 367–368, 374–376, 290, 92, 897; 128/155, 156; 424/28, 362; 435/101, 823

[56] References Cited

U.S. PATENT DOCUMENTS

| | | | |
|---|---|---|---|
| 3,419,006 | 12/1968 | King | 604/290 |
| 3,814,095 | 6/1974 | Lubens | 128/260 |
| 3,993,551 | 11/1976 | Assarsson | 204/159.14 |
| 4,289,824 | 9/1981 | Smith | 128/156 |
| 4,307,717 | 12/1981 | Hymes | 128/156 |
| 4,346,709 | 8/1982 | Schmitt | 604/897 |
| 4,373,519 | 2/1983 | Errede et al. | 128/156 |
| 4,378,431 | 3/1983 | Brown, Jr. | 435/101 |
| 4,423,101 | 12/1983 | Willstead | 128/156 |

Primary Examiner—C. Fred Rosenbaum
Assistant Examiner—Karen L. Kaechele
Attorney, Agent, or Firm—Wayne R. Eberhardt

[57] ABSTRACT

Liquid loaded pads useful as wound and burn dressings are prepared from pellicles of microbially-produced cellulose obtained, for example, by culturing *Acetobacter xylinum*. A pellicle having a thickness from about 0.1 to 15 millimeters or greater is processed to replace the culture medium with water or other physiologically compatible liquid. The liquid-loaded pellicle is sterilized prior to its use as a dressing or in other medical applications.

26 Claims, 5 Drawing Figures

LIQUID LOADED PAD FOR MEDICAL APPLICATIONS

FIELD OF INVENTION

This invention relates to a novel liquid carrying material for medical applications, and more particularly to a sterile pad comprising a pellicle of microbially-produced cellulose loaded or wetted with a physiologically-acceptable liquid useful as a wound dressing, treatment pad, wipe and the like, and to a method for preparing such material.

BACKGROUND OF THE INVENTION

A wide variety of products are currently available in the medical field for use as dressings in treating surgical incisions, abrasions, and burns, and as an aid in the treatment of a variety of dermatological skin disorders. Plain and medicated gauze-type dressings are widely employed in hospitals after major surgery and also in the home for minor accidental injuries. However, in spite of their wide acceptance, the gauze-type dressings are not without their disadvantages. For instance, frequent changes of such dressings are necessary in order to observe the healing process and to apply medication. Such changes are often accompanied by discomfort to the patient since some adherence to the wound or wound exudate normally occurs. Moreover, the gauze-type dressings do not protect the wound from extraneous bacteria nor do they control the proper moisture balance favorable to healing.

More recently, various polymeric materials have been investigated for use in the treatment of wounds, burns, and other skin disorders. For example, collagen, polyvinyl alcohol, gelatin, and a wide variety of polymeric materials have been disclosed in the literature as being useful in the treatment of accidental and surgical wounds. Hydrophilic polymer gels of polyethylene oxide and their use as wound dressings are described in U.S. Pat. No. 3,419,006 and suggested to be particularly useful in the treatment of burns, surgical and accidental injuries to the skin and eyes, and in a variety of dermatological applications. These gel dressings are alleged to provide a barrier to bacteria and viruses, to be permeable to vapors and gases while being impermeable to fluids, and to control the moisture environment of the wound.

Gauze pads wetted with physiologically acceptable fluids such as glycerol have been suggested for use as tissue drapes to prevent exposed organs from surface drying during extended surgical procedures. Gauze pads impregnated with antibacterial agents may be used as wipes to clean and disinfect or otherwise treat skin areas. Gauze, however, is not lint-free, and the deposition of lint on treated surfaces is considered undesirable in many situations.

The present invention relates to a liquid-loaded material useful as a wound dressing, surgical wipe, treatment pad, burn bandage, tissue/organ drape, and the like. Materials of the present invention comprise a pellicle of microbially-produced cellulose loaded with a physiologically-acceptable liquid and sterilized prior to use. One microbial agent particularly useful for preparing the dressings of the present invention is *Acetobacter xylinum* (A.x.). For purposes of understanding the present invention, the following is a brief description of the mechanism of cellulose production by A.x.

*Acetobacter xylinum* is a widely distributed, aerobic, gram-negative bacterium which converts glucose to cellulose and which can be found occurring naturally in fermenting sweet plant juices or rotting sugary fruits or vegetables. The naturally occurring A.x. bacteria includes mixtures of strains which vary in degree of cellulose producing efficiency. Bacteriological selection of high growth cellulose-producing strains is possible, and purified strains of A.x. such as strain number ATCC 23769 are available from such sources such as the American Type Culture Collection.

*Acetobacter xylinum* has been studied by numerous investigators whose interests have centered mainly on its cellulose generating mechanism. The major underlying scientific impetus throughout previous years of study has been that an understanding of cellulose formation in the simpler A.x. (prokaryotic) system would provide improved insight into cellulose formation from eukaryotic cells (sources of cotton, wood or paper products). The A.x. cellulose generating mechanism, however, has proven sufficiently complex that its exact biochemical sequence has not yet been fully elucidated, even though major insights have been achieved recently into the mechanics of cellulose extrusion from A.x.

*Acetobacter xylinum* is a rod-shaped bacterium having approximate dimensions of 3 $\mu M \times 0.6$ $\mu M$. The linear extension rate for cellulose growth is on the order of 1-2.5 $\mu M$/minute which corresponds to 1.5-3.5×10$^8$ glucose units processed per cell hour. Arranged at the bacterial surface, external to the plasma membrane, are typically 46 stationary synthesis sites for cellulose. The sites are arranged in two closely spaced lines of 23 sites each, and this double row lies parallel with the long axis of the bacterium. The sites are about 120 Å–150 Å in diameter and 35 Å in depth. Multiple poly-B-1,4-glucan chains (cellulose) issuing from each of the 46 sites combine to form individual microfibril ribbons about 1.6 $\eta M \times 5.8$ $\eta M$ in cross section. Very near the bacterial surface, the 46 microfibrils assemble into a single fibril which lies parallel to the bacterial surface and grows outward from the end of the bacterium. Thus, one bacterium typically produces one fibril of cellulose about 3.2 $\eta M \times 133$ $\eta M$ in cross section consisting of 46 microfibrils composed of multiple poly-B-1,4-glucan chains.

Extrusion of cellulose by A.x. is continuous and even occurs during cell division. The length of the cellulose fibril produced under ideal growing conditions is therefore limited only by the life span of the cellulose-producing bacteria. Fibril length can be controlled, however, by intermittent agitation of the growth medium. Still medium allows production of continuous fibril lengths while agitation breaks the bacterium away from the cellulose fibril at the 46 extrusion sites. Thus, intermittent agitation produces fibrils of finite length, which is determined by the linear extension rate and time between agitative shearing of the fibril from the bacterial surface.

Production of cellulose by A.x. typically involves bacterial activity at the air/liquid-medium interface. Each bacterium produces one fibril and the random intertwining of the fibrils results in a gelatinous, liquid-swollen structure known as a pellicle. Pellicle formation at the air/liquid interface is such that new cellulose is formed on top of existing cellulose, such that the existing cellulose is forced downward into the growth media. As a result, material placed lightly onto the liquid-medium surface becomes engulfed in pellicle and descends into the liquid-medium as more pellicle is formed. In this way, formation of cellulose pellicle is from the top down so that pellicle formation is analogous to formation of peat moss bog.

Cellulose fibrils formed by A.x. are much smaller than cellulose fibers from standard pulping of wood as seen from the following data:

| Source | Cellulose Fiber Dimensions | |
| --- | --- | --- |
|  | Length | Width |
| A.x. cellulose | "infinite" | $1.33 \times 10^{-4}$ mm |
| Birch | 0.8–1.6 mm | $1.4$–$4.0 \times 10^{-2}$ mm |
| Pine | 2.6–4.4 mm | $3.0$–$7.5 \times 10^{-2}$ mm |

It is accordingly an object of the present invention to provide a novel liquid loaded material for medical applications. A further object is to provide a wound dressing which is capable of cooling the skin surface and is accordingly particularly useful in the treatment of burns or other accidental injury to the skin surface. A still further object is to provide a novel treatment pad or wound dressing having one or more medicaments and/or additives incorporated therein. A still further object is to provide a wet sterile sheet-like material having exceptional strength and excellent handling and drape characteristics which allow the material to conform to the surface of the wound. A further object of the invention is to provide a novel dressing that can either supply moisture to the wound site or absorb exudate generated by the wound. A still further object of the present invention is to provide a process for the preparation of the aforementioned novel liquid loaded materials. These and other objects will readily become apparent to those skilled in the art in view of the teachings hereinafter set forth.

SUMMARY OF THE INVENTION

The materials of the present invention comprise a liquid loaded pad of microbially produced cellulose, particularly cellulose produced from the culture of *Acetobacter xylinum* (A.x.). The bacterium is cultured at the surface of a nutrient medium to form a coherent pellicle having a thickness from about 0.1 millimeter to about 15 millimeters or more. The pellicle is removed from the nutrient, treated with sodium hydroxide or other agent to remove the bacterium, neutralized, and washed with water to obtain a water-loaded pellicle of microbial cellulose. The pellicle thus formed has a coherent, dimensionally stable structure which may be cut to any desired size, sterilized by heat or irradiation and used as a dressing for burns or other skin injury. In another embodiment, the water may be exchanged with glycerol or other physiologically compatible liquid, and/or medicaments may be incorporated prior to sterilization and use. The liquid-loaded pellicle is packaged in a sterile, moisture-impervious container for long-term storage.

DETAILED DESCRIPTION OF THE INVENTION

Figure 1:
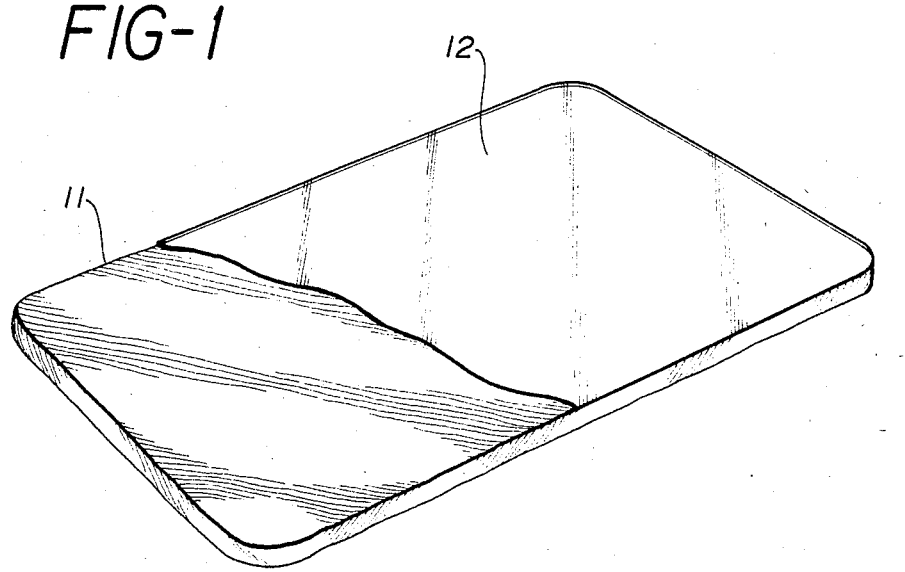
FIG. 1 is a view in perspective of one embodiment of a medical dressing according to the present invention.

In preparing the wound dressings of the present invention, A.x. microorganisms are cultured in a liquid nutrient medium at an initial pH of about 6 and at a temperature of from about 15° to 35° C., most preferably from 20° to 28° C. In order to obtain the coherent gel-like material desired for a wound dressing or other medical applications, it is essential that the culturing medium remain substantially motionless during the culturing period which may be from a matter of a few hours for a thin membrane of 0.1 millimeter thickness to several days or weeks for a pellicle having a thickness of 15 millimeters or greater.

The culturing medium is preferably based on glucose or other carbohydrate composition. As reported in "Synthesis of Cellulose by Resting Cells of *Acetobacter xylinum*", Nature, 159, (Jan. 11, 1947), rapid cellulose production was observed in culture media based on fructose, mannitol, and sorbitol as well as glucose. Slower growth rates were observed with glycerol, galactose, lactose, sucrose, and maltose. Zero growth was observed using sorbose, mannose, cellobiose, erythritol, ethanol, and acetate. However, good production of cellulose from a nutrient medium based on "cellooligosaccharides" such as cellobiose was reported in Japanese Patent Application No. 379-1979.

In the examples which follow, the culture medium which provided good results in growing cellulose from A.x. bacteria was that reported by Schramm and Hestrin, Biochem. J. 58, (1954), formulated as follows:

20 grams glucose
5 grams peptone
5 grams yeast extract
2.7 grams disodium phosphate
1.15 grams citric acid
1 liter distilled water The pH of the above formulation was adjusted to 6.0 with dilute HCl or NaOH as required, and the culture medium sterilized prior to use.

EXAMPLE 1

A sterile culture tray 50 by 50 by 10 cm was filled with sterile culture medium to a depth of 1.5 cm, inoculated with 95 cc of solution having a bacterial concentration of about $10^8$ A.x. per cc, covered and placed in a culture room at 20° C. where it remained undisturbed for 9 days. At the end of the culture period, a fibrous gel-like pellicle of bacterial cellulose had formed to a thickness of about 1.5 centimeters. The pellicle as removed from the tray was determined to contain about 10 grams cellulose and 1500 grams nutrient liquid. The pellicle was gently pressed between absorbent sheets to expel about 80% of the liquid content before treating with NaOH to remove entrapped A.x. bacteria.

The pressed pellicle was transferred to a solution of 3% NaOH where it was allowed to soak for 12 hours, during which time the pellicle reabsorbed about 70 percent of its original liquid content. While immersed in the NaOH solution, the pellicle was again pressed to expel about 80% of its liquid content and again allowed to reabsorb the NaOH solution. This procedure was repeated a third time, after which the pellicle was removed from the NaOH solution, pressed between absorbent sheets and transferred to a 3% solution of hydrochloric acid to neutralize the NaOH. The pressed pellicle was allowed to reabsorb the acid solution, then pressed between absorbent sheets and transferred to a bath of distilled water. The neutralized pellicle was repeatedly pressed and allowed to reabsorb in fresh, distilled water until substantially all of the sodium chloride salt was removed and the pH of the rinse water remained neutral.

The washed and neutralized water loaded pellicle retained about 60% of its original thickness of 1.5 centimeters and possessed excellent strength, handling and drape characteristics. The cellulose content of the saturated pellicle was determined to be about 40 g/M$^2$ and the water content about 3600 g/M$^2$. The pellicle was sterilizable by autoclaving or cobalt-60 radiation and was suitable for use as a sterile wet dressing for wounds or burns.

Liquid loaded dressings of the present invention control local wound environment, particularly moisture content, are substantially lint-free, and provide the benefits of gel dressings in a system free of potential chemical irritants such as unreacted monomers. The liquid holding capacity of the dressings of the present invention on a weight basis is far greater than that of conventional gauze dressing.

EXAMPLE 2

A water loaded pellicle prepared according to Example 1 was hand-pressed between absorbent sheets to reduce the water content to about 320 g/M$^2$ and to compress the pellicle into a thin, strong, wet, membrane-like sheet. The membrane had a thickness of less than about 1 mm and the weight ratio of liquid to cellulose in the membrane was approximately 8:1. Membranes having a weight ratio of liquid to cellulose in the range of from about 2:1 to 20:1 may be prepared in a similar manner. The compressed material is suitable for use as a protective wound covering or surgical wipe. When applied to wounds and covered with an occlusive backing film, such membranes have a capacity to absorb large quantities of wound exudate.

EXAMPLE 3

Compressed, membrane-like sheets prepared according to Example 2 were immersed in water, water/glycerine or saline, whereupon they recovered about 70% of their original liquid content and thickness. When placed on a skin surface, these dressings demonstrated a cooling effect due to evaporation of the liquid and were suitable for use as burn dressings. The reconstituted material was also suitable for use as a tissue/organ drape to prevent drying of exposed organs or tissue during extended surgical procedures.

EXAMPLE 4

The method of Example 2 was repeated except the membrane-like sheet material was partially reconstituted with glycerol in one case and with polyethylene glycol (MW 400) in a second case. The resulting product in each case contained about 2000 g/M$^2$ liquid, was strong and flexible with good handle and drape, and did not dry out when exposed to air. Each of the samples was transparent to an extent permitting visual examination of skin condition through the dressing. The material was substantially lint-free and was suitable for use as a general purpose dressing.

EXAMPLE 5

A water-loaded pellicle prepared according to Example 1 was allowed to air dry to form a thin, flexible sheet. The sheet was then immersed in glycerol whereupon it regained about 5% of its original liquid content. The resulting material was thin, strong and suitable for use as a wound covering.

EXAMPLE 6

The method of Example 2 was repeated except the membrane-like sheet material was reconstituted with an aqueous solution of 10% polyvinylpyrrolidone. After the membrane had recovered about 70% of its original liquid content, the pellicle was removed from the PVP solution and allowed to air dry to about 50% of its initial reconstituted weight. The concentration of PVP retained within the pellicle was thereby increased to about 20% of the liquid content. The pellicle was thereupon exposed to electron beam radiation at a dose of 2.5 megarads to crosslink the PVP solution and form a gel within the pellicle. The resulting product was strong and flexible and suitable for use as a wound or burn dressing. Similar results are obtained by substituting other water soluble, crosslinkable polymers or monomers for the PVP such as, for example, polyethylene oxide or sodium acrylate.

EXAMPLE 7

The method of Example 2 was repeated except the membrane-like sheet was reconstituted with 1% silver sulfadiazine (SSD) ointment. The compressed pellicle was immersed in SSD ointment which had been warmed to fluid state until the liquid content of the pellicle had increased to about 1000 g/M$^2$. The impregnation with SSD ointment was conducted in a darkroom and the resulting product was packaged in a light proof, moisture-impervious aluminum foil packet and was suitable for use as a burn dressing. A similar product is obtained by impregnating the membrane-like sheet with an aqueous solution of zinc sulfadiazine. In another embodiment, the membrane-like sheet may be surface-coated with silver sulfadiazine powder so that the antiseptic is applied directly to the burn site.

EXAMPLE 8

The method of Example 2 was repeated except the membrane-like sheet material was partially reconstituted with water to a loading of 2000 g/M$^2$. The water-loaded pellicle was immersed in melted petrolatum at a temperature of 100° C. for 1 hour. The pellicle was thereupon removed and allowed to drain. The resulting product was a petrolatum-coated dressing having a water core and had a reduced tendency to adhere to wounds.

EXAMPLE 9

A water-loaded pellicle was prepared according to Example 1, except that the lid of the culture tray was provided with downward projecting cylindrical rods attached in a square pattern. The rods were ⅛ inch in diameter and were set at the corners of a ⅜ inch square pattern. The free end of each rod extended perpendicular to the lid a sufficient distance so that when the culture tray was loaded with medium and the lid put in place, the rods penetrated the surface of the medium. The pellicle produced in such an apparatus was perforated with holes corresponding to the pattern of the rods. Treatment of the pellicle as in Example 8 resulted in a structure which, when used as a dressing on exudating wounds, allowed movement of the fluid through the holes and into an absorbent secondary dressing.

Each of the above examples illustrates the preparation of a liquid loaded material from a pellicle of microbially-produced cellulose wherein the nutrient medium initially entrapped in the pellicle during its formation is replaced with a physiologically-acceptable liquid. The weight ratio of liquid to cellulose in such pellicle is typically from about 5:1 to 100:1, and in some circumstances may be 150:1 or higher. The liquid may be distilled water, saline, glycerol, polyethylene glycol, isopropanol and other lower alcohols, petrolatum, mixtures thereof, or any other physiologically acceptable material. In each case, the liquid loaded pad is sterilized prior to use in a medical application using conventional, appropriate means such as autoclaving or radiation.

The NaOH treatment described in Example 1 for removal of entrapped A.x. bacteria and bacterial residue from the pellicle may be modified with equivalent results. For example, the pellicle may be boiled in a 1 to 10% solution of NaOH or KOH for up to 1 hour or more to effectively remove the bacteria, then neutralized with hydrochloric, acetic, or other suitable acid and washed with distilled water as described. Alternatively, the A.x. bacteria may be removed from the pellicle by treatment with other agents such as trichloroacetic acid, potassium hydroxide, and the like, or rendered unreactive by crosslinking with gluteraldehyde, formaldehyde, or dialdehyde starch.

Some treatment to remove entrapped bacteria is desirable when preparing materials for surgical uses, particularly for use as moist tissue/organ drapes, since the untreated pellicle contains endotoxins resulting from the rupture of the bacteria cells which, if absorbed by a living organism in sufficient quantities, would cause a pyrogenic reaction. In the pellicles produced by A.x. bacteria, the concentration of lipopolysaccharide endotoxins in the final, neutralized and washed material prepared according to Example 1 is from about 1 to 50 nanograms per gram of material. By contrast, the endotoxin content of pellicle which has been mechanically worked to rupture the A.x. cells, but not chemically treated to remove the bacteria, may be 30,000 nanograms per gram of material or higher.

In pyrogen-sensitive applications, care must be taken to assure not only that the bacterial endotoxins are removed from the pellicle during processing, but that pellicle is subsequently handled under pyrogen-free conditions and loaded with pyrogen free liquid materials.

The treatment to remove entrapped bacteria is optional in preparing certain products of the present invention where no harmful consequences result if this step is omitted, as for example, in the preparation of skin wipes or surface dressings. In any event, the A.x. bacteria would, of course, be killed along with any harmful bacteria which might be present when the pellicle is sterilized as required for medical use.

The glycerol-loaded material of Example 4 was sterilized in a steam autoclave and evaluated as a wound dressing in animal studies involving full thickness dorsal incision on guinea pigs. In this test, the dorsal area of a guinea pig is shaved and a full thickness section of skin about 2.5 centimeters in diameter is surgically removed. A dressing is applied and the extent of wound contraction after 8 days is determined. In the case of the material of Example 4, wound contraction after 8 days was about 50% which was equivalent to that generally obtained with currently available occlusive surgical dressings.

Turning now to the drawings, there is illustrated in FIG. 1 a pad for medical application comprising a sterile liquid-loaded pellicle 11 covered on one side with a moisture impervious occlusive backing sheet 12 such as a film of polyethylene. The occlusive backing sheet is an optional feature which may be present or omitted depending upon the intended application. For example, the film is typically omitted when the pad is to be used as a surgical wipe, and is typically present when the pad contains a medicament and is to be used for treating a wound.

Figure 2:
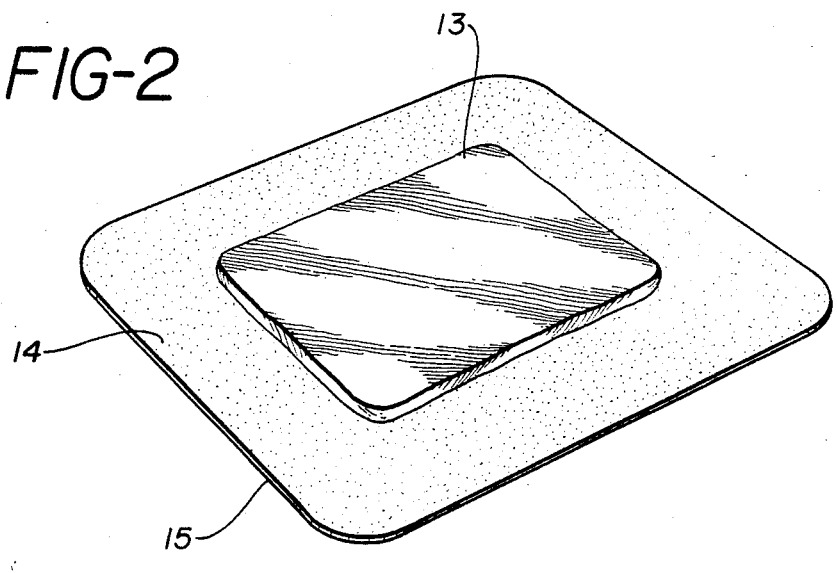
FIG. 2 is a view in perspective of an island dressing of the present invention.

FIG. 2 illustrates an island dressing comprising a liquid-loaded pellicle 13 centered on a backing film 15 which extends beyond the borders of the pellicle. The backing film is coated with a pressure-sensitive adhesive 14 around the perimeter of the pellicle which allows the dressing to be adhesively secured to the patient at the wound site.

Figure 3:
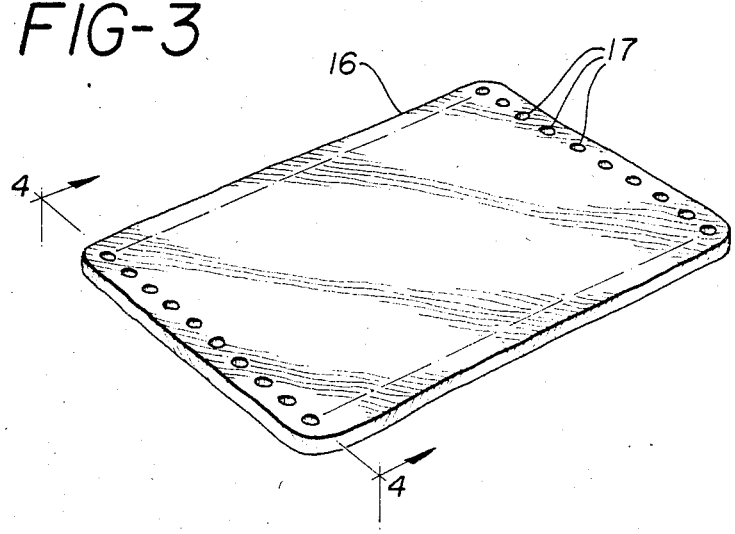
FIG. 3 is a view in perspective of another embodiment of a medical dressing according to the present invention.
Figure 4:
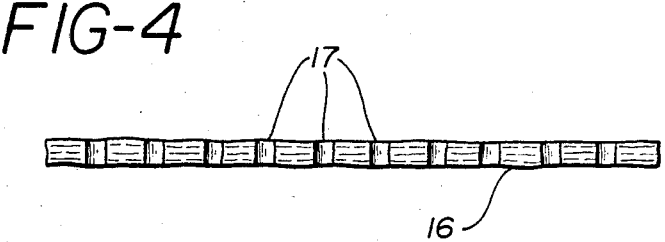
FIG. 4 is a view in cross-section of the dressing of FIG. 3.

FIGS. 3 and 4 illustrate a medical dressing which contains a plurality of holes 17 extending through pellicle 16 in order to provide for the discharge of fluids from heavily exudating wounds. Such pads are used as the primary wound dressing under a secondary absorbent dressing which may be changed from time to time without disturbing the primary dressing.

Figure 5:
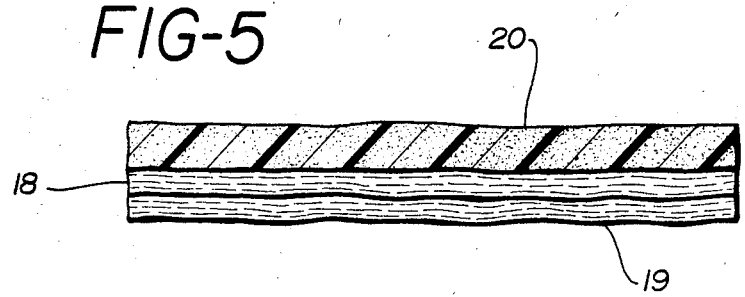
FIG. 5 is a view in perspective of a cold pack burn dressing according to the present invention.

FIG. 5 illustrates a cold pack for use as a burn dressing which comprises a double layer of liquid-loaded pellicle 18 and 19 covered by an insulating mat 20. The dressing is chilled prior to use and applied directly to the surface of the burn. Initial cooling is provided by the temperature differential and further evaporative cooling is obtained by removing the insulating cover and allowing the liquid, usually sterile water or saline, to evaporate from the pellicle.

Due to the permeability and biological inertness of the materials of this invention, they are particularly suited for the incorporation therein of a wide variety of chemotherapeutic agents, medicinal agents and additives. For instance, the dressings can contain topical anesthetics such as butamben picrate, lidocaine hydrochloride, piperocaine hydrochloride and the like; bacteriostatic agents such as silver nitrate (0.5% solution), sulfa drugs, for example, 10% suspension of p-aminomethylbenzene sulfonamide in a water dispersible cream, benzalkonium chloride and the like; antibiotics such as bacitracin, neomycin, aureomycin, tetracycline, penicillin, polymyxin streptomycin, signemycin, erthromycin, oleandomycin, and the like; topical steroids such as prednisone, dexamethasone, hydrocortisone and the like; enzymes such as collagenase, fibrinolysin, desoxyribonuclease and the like; coagulants and anticoagulants; antifungal agents, such as isopropanol, nystatin, miconazole, ketoconazole, tolnaftate and the like. Non-water soluble medicaments such as silver sulfadiazine are preferably dispersed in nonaqueous ointment bases which may be liquified to impregnate the pellicle as hereinbefore described.

The quantity of the aforementioned medicinal agents, chemotherapeutic agents or additives which can be incorporated into the liquid loaded materials will, of course, be dependent upon the particular agent, its solubility, and the presence of other additives. In general, however, the agents will be employed in a therapeutic amount. This can range from about, 0.0001% and lower, upwards to about 40% and higher by weight. A unique feature of the present materials is that additional or different chemotherapeutic agents or medicaments can be added to the dressing while in place and transported to the site of the wound by diffusion through the material. Hence, it is possible either by incorporating medicaments directly into the material before use, or applying medicaments to the material while in place over the injured area, to provide controlled supply of medication to the wound site. As a result of the high liquid-holding capacity of the products of the present invention, materials loaded with a medicament carry a greater amount of the active agent to the treatment site than comparable conventional dressings.

The liquid loaded materials of the present invention are essentially lint-free and may be used with good results as skin and surgical wipes. Because the materials contain a high liquid content, a wipe of a given size contains a greater amount of available liquid than, for example, a wetted gauze sponge, and may effectively wipe a greater area with no deposition of lint or gauze fragments. Pads to be used as wipes are preferably loaded with isopropanol.

The liquid loaded materials of the present invention may be used as wet dressings in combination with an occlusive film backing for some applications. For example, in the case of an ulcer dressing which is required to provide a wound environment conducive to the growth of new tissue, the dressing should provide a source of moisture over an extended period of time and ensure an antibacterial environment. A dressing of the present invention loaded with an aqueous solution containing an antimicrobial agent may be applied to such an ulcer and covered with an occlusive film backing to prevent evaporation of moisture from the dressing. A wide variety of films are suitable for use as backings for a wound dressing including, for example, polyvinylidene chloride, polyethylene, polypropylene, polyethylene terephthalate, polyamides, polyvinyl chloride, cellulose acetate and derivatives thereof, polydimethyl butadiene, polyurethanes, polyvinyl alcohol, silicone rubbers, polyacrylic acid, and the like. The film may be attached to the liquid loaded material by the surface tension of the liquid or through the use of adhesives or mechanical fastening if preferred. In one embodiment of the invention, the backing film may extend beyond the area of the dressing and be adhesive coated to form an island dressing which may be secured directly to the skin of the patient.

Liquid loaded materials intended specifically for use as burn dressing should provide for evaporation from the dressing to provide a cooling effect over the wound area. Such dressings are accordingly loaded with an evaporative liquid which may be water, saline or a water/glycerol or water/polyethylene glycol solution and are not covered with an occlusive backing film during use. The products of this invention may also be produced in long lengths for use as burn bandages, and in large sheets, i.e., 3 by 5 feet or greater, for use as burn blankets.

Cold packs for burns, as distinguished from burn dressings may be provided with a removable insulating backing since cold packs are chilled prior to application and do not initially depend upon evaporative cooling. The cooling effect of the cold pack may be extended by removing the backing and allowing evaporative cooling to take place after the initial cooling capacity due to thermal differential has been exhausted. Cold packs additionally may utilize thicker or multiple layers of liquid loaded material to increase their heat capacity.

Liquid loaded materials according to the present invention may be used as long-term coverings for severe burns and certain other wounds. In this application, a thin dressing of this invention from 0.1 to 5 millimeters thick is placed immediately over the wound and a second dressing of this invention containing medicaments or other wound treating agents is placed over the primary dressing. Since the medicaments will migrate through the primary dressing to the wound surface, the secondary dressing may be changed from time to time to renew the medicament treatment while the healing process of the wound is observed through the primary dressing which is not disturbed.

While the products of the present invention inherently have high strength, various reinforcing materials such as random or carded fibers, plastic net, reticulated plastic film, open weave fabrics and fabric mesh may be incorporated in the dressing if desired. For example, nylon gauze, rayon net, Dacron or cellulose mesh or reticulated polyethylene can be embedded in the pellicle while the pellicle is being formed. The sterile reinforcing material is placed carefully on the surface of the nutrient medium of an active culture of A.x. bacterial containing a thin pellicle of bacterial cellulose, with care being taken not to break the surface tension of the nutrient medium. As the production of cellulose continues, the reinforcing material is encapsulated by newly formed cellulose and carried down into the nutrient medium as new cellulose is produced at the surface of the nutrient medium.

An additional feature of the wet dressings of the present invention is their ability to absorb large quantities of fluid from the wound site when the dressing is applied in a less than saturated condition. In the case of burn dressings, moisture evaporating from the dressing will tend to be replaced by fluids exuding from the burn site. In other cases, a dressing which has been compressed to expel its normal liquid content or which has been partially predried may be used directly to absorb wound exudate. Preferably, such a dressing is covered with an occulsive film to prevent the dressing from drying out while in place over the wound.

When a dressing of this invention is allowed to dry while in place over a wound or burn site, the dressing adheres to the wound and upon removal, provides a degree of debridement which assists in cleansing the wound site. When it is desirable to avoid adherence, the dressing should be removed before drying, or should be loaded with a nonadherent material such as petrolatum as described in Example 8.

The liquid loaded materials of the present invention are sterilized prior to use by any appropriate method such as auto-claving or irradiation with cobalt-60 or electron beam. The materials are packaged in sterile hermetically sealed moisture-proof containers. Most preferably, the materials are heat sealed in packages constructed of aluminum foil laminated with a heat sealable polymeric film such as polyethylene, and sterilized in the package by irradiation in accordance with conventional methods for packaging surgical products. Sterile materials may be stored for extended periods of time with no adverse effect.

As is apparent from the preceding description and examples, the present invention is directed to sterile, liquid carrying pads or sheets of microbially-produced cellulose. The products may be constructed in a variety of shapes, sizes, and thicknesses and loaded with a variety of physiologically-acceptable liquids and medicaments to accommodate the requirements of any particular application. Additionally, the materials may be used in combination with internal reinforcements or external backing films and may be used as the pad portion of island dressings which include adhesive attachment means. Many other variations and the details of construction and composition will be apparent to those skilled in the art and such variations are contemplated within the broad scope of the present invention.

We claim:

1. A liquid loaded pad for medical applications comprising a fibrous mass of microbially-produced cellulose fibrils and a sterile, physiologically-acceptable liquid retained within the interstices of said fibrous mass, said fibrous mass having a coherent and dimensionally stable structure.

2. A pad of claim 1 wherein the weight ratio of liquid to cellulose in said fibrous mass is from about 5:1 to 150:1.

3. A pad of claim 1 wherein said physiologically-acceptable liquid is selected from the group consisting of distilled water, saline, glycerol, polyethylene glycol, lower alcohols, and mixtures thereof.

4. A pad of claim 3 wherein said liquid is pyrogen-free.

5. A pad of claim 1 wherein said physiologically-acceptable liquid is an aqueous gel of a crosslinked polymer.

6. A pad of claim 5 wherein said polymer is polyethylene oxide, polyvinylpyrrolidone or sodium acrylate.

7. A pad of claim 1 wherein said physiologically-acceptable liquid includes a medicament.

8. A pad of claim 1 wherein said pellicle is substantially free of the microbial agents responsible for the production of said cellulose.

9. A pad of claim 1 including a moisture-impervious, occlusive backing sheet.

10. A pad of claim 9 wherein said occlusive backing sheet extends beyond the edge of said fibrous mass to form an island dressing.

11. A pad of claim 10 wherein that portion of said backing sheet extending beyond the edge of said fibrous mass is adhesive-coated.

12. A pad of claim 1 wherein said fibrous mass has a thickness from about 0.1 millimeter to 15 millimeters.

13. A pad of claim 1 having a plurality of openings extending therethrough.

14. A wound, burn dressing or tissue/organ drape comprising a pad of claim 1.

15. A surgical wipe comprising a pad of claim 13.

16. A pad of claim 1 wherein said fibrous mass is coated with petrolatum.

17. A liquid loaded pad comprising a compressed pellicle of microbially-produced cellulose fibrils and a sterile, physiologically-acceptable liquid retained within the interstices of said compressed pellicle, said pellicle having a coherent and dimensionally stable structure with a thickness of less than about 1 millimeter.

18. A pad of claim 17 wherein the weight ratio of liquid to cellulose in said pellicle is from about 2:1 to 20:1.

19. A pad of claim 17 wherein said physiologically-acceptable liquid is selected from the group consisting of distilled water, saline, glycerol, polyethylene glycol, lower alcohols, and mixtures thereof.

20. A pad of claim 19 wherein said liquid is pyrogen-free.

21. A pad of claim 17 wherein said physiologically-acceptable liquid includes a medicament.

22. A pad of claim 17 including a moisture-impervious, occlusive backing sheet.

23. A burn dressing of claim 21 wherein said physiologically-acceptable liquid is selected from the group consisting of water, saline, water/polyethylene glycol and water/glycerol solutions.

24. A dressing of claim 23 wherein said liquid is pyrogen-free.

25. A burn dressing comprising a fibrous mass of microbially-produced cellulose fibrils and a sterile, volatile, physiologically-acceptable liquid retained within the interstices of said fibrous mass, said fibrous mass having a coherent and dimensionally stable structure.

26. A cold pack for treating burns comprising a fibrous mass of microbially-produced cellulose fibrils, a sterile, physiologically-acceptable liquid retained within the interstices of said fibrous mass, and an insulating backing material on one side of said fibrous mass, said fibrous mass having a coherent and dimensionally stable structure independent of said insulating backing material.

* * * * *

UNITED STATES PATENT AND TRADEMARK OFFICE
CERTIFICATE OF CORRECTION

PATENT NO. : 4,588,400
DATED : May 13, 1986
INVENTOR(S) : David F. Ring, Wilson Nashed, Thurman Dow It is certified that error appears in the above-identified patent and that said Letters Patent is hereby corrected as shown below:

Claim 8, column 11, line 35: "pellicle" should read
-- fibrous mass --.

Signed and Sealed this

Nineteenth Day of August 1986

[SEAL]

Attest:

DONALD J. QUIGG

Attesting Officer

Commissioner of Patents and Trademarks